US006866819B1

(12) United States Patent
Chandra et al.

(10) Patent No.: US 6,866,819 B1
(45) Date of Patent: Mar. 15, 2005

(54) SENSOR FOR DETECTING SMALL CONCENTRATIONS OF A TARGET MATTER

(75) Inventors: Dipankar Chandra, Richardson, TX (US); Athanasios J. Syllaios, Richardson, TX (US)

(73) Assignee: Raytheon Company, Waltham, MA (US)

( * ) Notice: Subject to any disclaimer, the term of this patent is extended or adjusted under 35 U.S.C. 154(b) by 236 days.

(21) Appl. No.: 10/006,891

(22) Filed: Nov. 13, 2001

(51) Int. Cl.[7] .................. G01N 21/00; G01N 31/22; G01N 15/06; G01N 33/00; G01N 33/48

(52) U.S. Cl. .................. 422/50; 422/56; 422/57; 422/61; 422/68.1; 422/82.01; 422/82.02; 422/83; 422/88; 422/94; 422/96; 422/97; 422/98; 436/43; 436/149; 436/151; 73/1.01; 73/1.02; 73/23.2

(58) Field of Search .................. 422/50, 56, 57, 422/61, 68.1, 82.01, 82.02, 83, 88, 94, 96, 97, 98; 436/43, 149, 151; 73/1.01, 1.02, 23.2

(56) References Cited

U.S. PATENT DOCUMENTS

| 3,631,436 | A |   | 12/1971 | Taguchi .................. 340/237 |
|---|---|---|---|---|
| 4,549,427 | A |   | 10/1985 | Kolesar, Jr. .................. 73/23 |
| 4,809,552 | A |   | 3/1989 | Johnson .................. 73/517 |
| 4,899,125 | A |   | 2/1990 | Kurtz .................. 338/2 |
| 4,951,510 | A |   | 8/1990 | Holm-Kennedy et al. .......... 73/862.04 |
| 5,028,394 | A |   | 7/1991 | Lowell, Jr. et al. .......... 422/58 |
| 5,417,100 | A |   | 5/1995 | Miller et al. .................. 73/31.02 |
| 5,512,882 | A |   | 4/1996 | Stetter et al. .................. 340/632 |
| 5,559,358 | A |   | 9/1996 | Burns et al. .................. 257/431 |
| 5,563,341 | A |   | 10/1996 | Fenner et al. ............ 73/335.11 |
| 5,583,286 | A |   | 12/1996 | Matsuyama .................. 73/105 |
| 5,780,727 | A |   | 7/1998 | Gimzewski et al. .......... 73/105 |
| 5,852,229 | A | * | 12/1998 | Josse et al. .................. 73/24.06 |
| 6,016,686 | A |   | 1/2000 | Thundat .................. 73/23.2 |
| 6,545,384 | B1 | * | 4/2003 | Pelrine et al. .............. 310/309 |
| 6,623,620 | B2 | * | 9/2003 | Lai et al. .................. 205/786.5 |

FOREIGN PATENT DOCUMENTS

| DE | 2244659 | 3/1974 | ............. F02D/5/00 |
|---|---|---|---|
| EP | 60250259 | 10/1985 | |
| EP | 445508 A2 | 9/1991 | .......... G01P/13/02 |
| EP | 0821228 A1 | 1/1998 | .......... G01N/27/12 |
| GB | 1252433 | 11/1971 | ............. G01P/5/04 |
| WO | 9428372 | 12/1994 | ............. G01B/7/16 |
| WO | 9705824 A | 2/1997 | .......... A61B/5/087 |
| WO | WO 00/39570 | 7/2000 | .......... G01P/27/00 |

OTHER PUBLICATIONS

International Search Report for PCT/US99/30540, Aug. 9, 2000.

(List continued on next page.)

*Primary Examiner*—Jill Warden
*Assistant Examiner*—Brian Sines
(74) *Attorney, Agent, or Firm*—Baker Botts L.L.P.

(57) ABSTRACT

A sensor for detecting a target matter includes a chemical sensitive layer that is operable to react when exposed to the target matter and a piezoresistive material coupled to the chemical sensitive layer. The chemical sensitive layer is configured such that the reaction of the target matter with the chemical sensitive layer creates an interfacial tension at the interface of the chemical sensitive layer and the piezoresistive material that changes the electrical resistance of the piezoresistive material. However, the chemical sensitive layer is configured such that the reaction of the target matter with the chemical sensitive layer does not affect the bulk properties of the chemical sensitive layer enough to change the electrical resistance of the piezoresistive material. The sensor also includes an electrical circuit coupled to the piezoresistive material that is operable to detect the change in the electrical resistance of the piezoresistive material due to the interfacial tension.

22 Claims, 2 Drawing Sheets

OTHER PUBLICATIONS

International Search Report for PCT/US99/30661, Apr. 17, 2000.

T. Nishimoto, S, Shoji and M. Esashi, "Buried piezoresistive sensors by means of MeV Ion Implantation" Sensors and Actuators A, CH, Elsevier Sequoia, S.A., Lausanne, vol. A43, No. 1/03, pp. 249–253, XP000454110, May 1, 1994.

L. N. Krause, et al., "Miniature Drag–Force Anemometer" I.S.A. Transactions, vol. 21, No. 1, 1982, pp. 37–44, XP002134780, Jan. 1, 1982.

S. M. Sze, "Semiconductor Sensors" a Wiley–Interscience Publication, pp 193–194, 358–361, 1994.

A. J. Ricco, G. C. Osbourn, R. M. Crooks, JW. Bartholomew, C. Xu and R.E. Allred "Interfacial Design and Chemical Sensing" Eds: T. E. Mallouk, D. J. Harrison, p. 264, ACS, Washington DC, 1994.

L.S. Darken, R. W. Gurry, M. B. Bever, "Physical Chemistry of Metals," McGraw–Hill Book Co., pp. 244–258, 1953.

J.W. Cahn and R.E. Hanneman, "Surface Tensions of Hi–V Compounds and Their Relationship to Spontaneous Bending of Thin Crystals," Eds: Surface Science 1, pp 387–398, 1963.

F. J. VonPreissig, "Applicability of the Classical Curvature–stress Relation for Thin Films on Plate Substrates," Eds: J. App. Phys. 66, pp 4262–4268, 1989.

M. Tortonese, R. C. Barrett and C.F. Quate, "Atomic Resolution with an Atomic Force Microscope Using Piezoresistive Detection," Eds: Appl. Phys. Lett. 62, pp 834–836, 1993.

P. Muller and R. Kern, "About the Measurement of Absolute Isotropic Surface Stress of Crystals," Eds: Surf. Sci. 301, pp. 386–398, 1994.

T. Thundat, E. A. Wachter, S. L. Sharp, and R.J. Warmack, "Detection of Mercury Vapor Using Resonating Microcantilevers," Eds: Appl. Phys. Lett 66, pp. 1695–1697, 1995.

G. Y. Chen, T. Thundat, E. A. Wachter, and R. J. Warmack, "Adsorption–Induced Surface Stress and Its Effects on Resonance Frequency of Microcantilevers," Eds: J. Appl. Phys. 77, pp. 3618–3622, 1995.

E. A. Wachter and T. Thundat, "Micromechanical Sensors for Chemical and Physical Measurements," Eds: Rev. Sci. Instrum. 66, pp 3662–3667, 1995.

T. Thundat, G. Y. Chen, R. J. Warmack, D. P. Allison and E. A. Wachter, "Vapor Detection Using Resonating Microcantilevers," Eds: Anal. Chem. pp. 519–521, 1995.

C. Battistoni, E. Bemporad, A. Galdikas, S. Kaciulis, G. Mattogno, S.Mickevicius and V. Olevano, "Interaction of Mercury Vapor with Thin Films of Gold," Eds: Appl. Surf. Sci. 103, pp. 107–111 XP002061342, 1996.

P.I. Ogden, G. Y. Chen, R. A. Steele, R. J. Warmack and T. Thundat, "Viscous Drag Measurements Utilizing Microfabricated Cantilevers," Eds: Appl. Phys. Lett. 68, pp. 3814–3816, 1996.

B. W. Chui, T. D. Stowe, Y.S. Ju, K. E. Goodson, T. W. Kenny, H. J. Mamin, B. D. Terris, R. P. Ried and D. Rugar, "Low–Stiffness Silicon Cantilevers with Integrated Heaters and Piezoresistive Sensors for High–Density AFM Thermomechanical Data Storage," Eds: J. Microelectromech. Syst. 7, pp. 69–78, 1998.

G.G. Stoney, "The Tension of Metallic Films Deposited by Electrolysis," Eds: Proceedings of the Royal Society of London, Ser. A, pp. 172–175, Sep. 1909.

A. Brenner and S. Senderoff, "Calculation of Stress in Electrodeposits from the Curvature of a Plated Strip," Eds: Journal of Research of the National Bureau of Standards, vol. 42, pp. 105–123, Feb. 1949.

R. F. Brebrick and A. J. Strauss, "Partial Pressures of Hg(g) and $Te_2(g)$ in Hg–Te System from Optical Densities," Eds: Journal of Physics and Chemistry of Solids vol. 26, pp. 989–1002, Jan. 1965.

W.R. Seitz, "Optical Sensors Based on Immobilized Reagents," Eds: A.F.P. Turner, et al, Oxford Science Publications, Oxford, pp. 599–616, 1987.

* cited by examiner

SENSOR FOR DETECTING SMALL CONCENTRATIONS OF A TARGET MATTER

TECHNICAL FIELD OF THE INVENTION

This invention relates generally to gas and chemical sensors and more particularly to a micro-electromechanical system for detecting very small concentrations of a target matter.

BACKGROUND OF THE INVENTION

A multitude of sensors are presently in use to detect various types of gases and chemical compounds. Such sensors range from the common household smoke detector to those designed to detect deadly nerve gases. Many of these applications require sensors that are sensitive and relatively small in size.

Current sensing and detection technologies have a number of drawbacks such as poor sensitivity and selectivity for the target matter, relatively long analysis times, lack of portability, and relatively high costs. For some applications, detection sensitivities in the part per trillion range (ppt) are needed, but few techniques even approach such sensitivity levels. For example, explosive sensors must be able to detect target matter such as TNT with below part per billion (ppb) sensitivity. Similarly, chemical agent sensors must exhibit sub-ppb sensitivity and be capable of distinguishing the nerve agent class (GA, GB, GD, GF, VX) and the blistering agent class (HD, L, T) of chemical agents. Present sensor technology generally does not offer the capability of sensing concentrations below the ppb range.

SUMMARY OF THE INVENTION

Accordingly, a need has arisen for a compact, light weight, low power, high sensitivity sensor capable of detecting chemical concentrations in gas and liquid phases with sub-ppb sensitivity. The present invention provides a sensor that addresses these needs.

According to one aspect of the present invention, a sensor for detecting a target matter includes a chemical sensitive layer that is operable to react when exposed to the target matter and a piezoresistive material coupled to the chemical sensitive layer. The chemical sensitive layer is configured such that the reaction of the target matter with the chemical sensitive layer creates an interfacial tension at the interface of the chemical sensitive layer and the piezoresistive material that changes the electrical resistance of the piezoresistive material. However, the chemical sensitive layer is configured such that the reaction of the target matter with the chemical sensitive layer does not affect the bulk properties of the chemical sensitive layer enough to change the electrical resistance of the piezoresistive material. The sensor also includes an electrical circuit coupled to the piezoresistive material that is operable to detect the change in the electrical resistance of the piezoresistive material due to the interfacial tension.

Embodiments of the invention provide numerous technical advantages. For example, sensors incorporating teachings of the present invention may be manufactured as micro-electromechanical systems (MEMS) for use in both microenvironments and normal environments. In one embodiment of the present invention, a MEMS chemical sensitive single crystal silicon cantilever design is used which has no moving parts, therefore making the embodiment simple and compact. Another technical advantage is the use of a chemical sensitive layer with selected sensitivity to specific gases, liquids, and chemical species, such that specific gases, liquids and chemical species interact preferentially and selectively with the chemical sensitive layer, imposing interfacial tension at the interface of the chemical sensitive layer and the piezoresistive material without a volume and/or structural change in the chemical sensitive layer or in the underlying membrane platform. No mass loading and no introduction of mechanical strain that can be measured needs to accompany these processes.

The use of this chemical sensitive layer in this manner in combination with a piezoresistive material allows for sub-ppt sensitivity. The sensitivity attainable is superior to sensitivities which would have been attainable if the target matter were required to react with the chemical sensitive layer to change its volume and/or its structure, and/or alter the mass loading of the platform since a higher quantity of the target matter would be required to attain the latter objectives. Further, enhancement of sensitivity is possible in embodiments of the invention that employ a continuously and dynamically balanced bridge where one or more resistors are precisely matched and balanced to the resistance of the piezoresistive material of the sensor. Therefore, particular embodiments employ a technique by which the resistance of a sensor piezoresistor and a variable resistor exactly match each other continuously. The variable resistor may be programmed using digital signal processing techniques to vary continuously and dynamically so as to remain equal to the sensor resistor.

Still further technical advantages of the present invention include the use of a chemical sensitive sensor platform and non-chemical sensitive reference platform pair to compensate for environmental transients. In addition, particular embodiments provide multi-channel capability to detect multiple types of gases, liquids or chemical species. Furthermore, sensors incorporating the present invention may be used in outdoor sensor networks and handheld applications due to their ruggedness, compactness, low weight, low power requirements, and low cost.

Sensors formed in accordance with particular embodiments may also be used for continuous monitoring of a target matter while remaining unsaturated during the usable lifetime of the sensor, since the target matter only interacts with the interface of the chemical sensitive layer and piezoresistive material in a certain manner without altering the volume and/or structural property of the chemical sensitive layer itself. The surface charge density of either the chemical sensitive layer or the piezoresistive material itself need not change during this interaction. Sensors incorporating teachings of the present invention are also capable of operating as stand alone sensors or as components of networked arrays of diverse sensors.

Other technical advantages may be readily apparent to those skilled in the art from the figures, description and claims included herein.

BRIEF DESCRIPTION OF THE DRAWINGS

For a more complete understanding of the present invention and the advantages thereof, reference is now made to the following descriptions taken in connection with the accompanying drawings in which.

DETAILED DESCRIPTION OF THE INVENTION

The following terms will be used throughout the application. Therefore, their definitions are provided here. In this application, the term "target matter" shall mean a gas, vapor, liquid, chemical species, or any other type of matter which is sought to be detected. In this application, the term "ppm" shall stand for "part per million". The phrase "part per million" shall mean that for every one million parts of a certain medium (i.e. air), there is only one part of the target matter. The "part" can be any representative amount of a substance, such as a molecule or a certain volume. Similarly, the terms "ppb" and "ppt" stand for "part per billion" and "part per trillion", respectively. The meaning of these phrases is clear from the meaning of "part per million", discussed above. Furthermore, in this application, the term "chemical sensitive" shall be used to described a substance that reacts to or is sensitive to a selected target matter.

Figure 1:
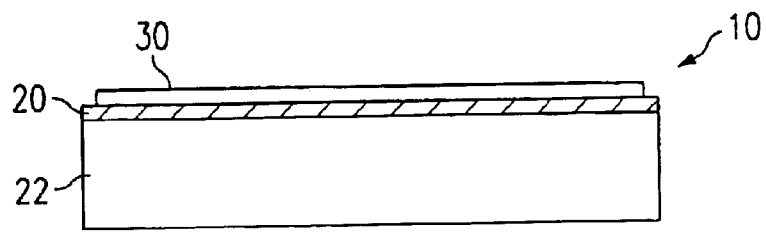
FIG. 1 is a schematic drawing in elevation showing an example sensor incorporating teachings of the present invention.
Figure 2:
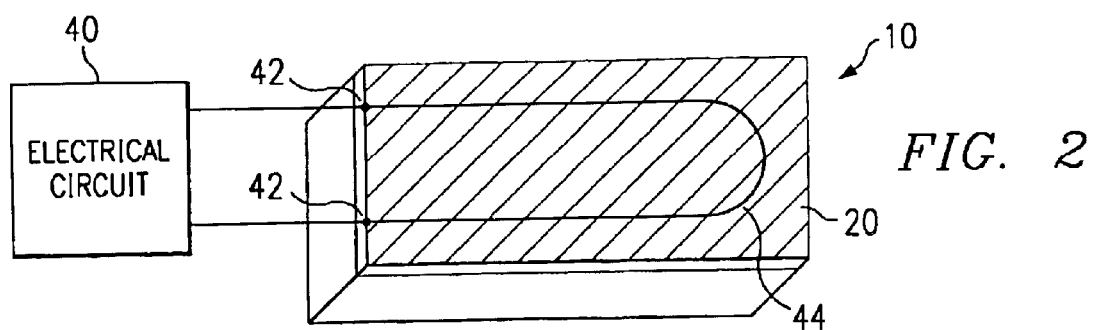
FIG. 2 is a schematic drawing showing an isometric view of the sensor of FIG. 1 and an electrical circuit for obtaining data from the sensor.

FIGS. 1 and 2 illustrate an example sensor 10 incorporating teachings of the present invention. This embodiment is simplified to show the three components of the invention and their operation. The first such component is a layer or other arrangement of a selected piezoresistive material 20. Piezoresistive material 20 experiences a change in resistance when an interfacial tension is created on its surface or on the surface of a layer applied to it. Piezoresistive material 20 may be layered on or implanted in a support medium 22, or it may stand alone.

The second such component is a chemical sensitive layer 30. Chemical sensitive layer 30 may be mechanically coupled or bonded to piezoresistive material 20 or formed by altering at least the surface of piezoresistive material 20 (for example, a surface of the piezoresistive material 20 may be doped to create a chemical sensitive layer 30 at the surface). Chemical sensitive layer 30 includes a material selected in such a manner as to react preferentially with a selected target matter. The target matter may be any appropriate matter that reacts with a particular type of chemical sensitive layer 30 so as to create an interfacial tension at the interface of chemical sensitive layer 30 and piezoresistive material 20 (which may then be detected due the resulting change in the resistance of piezoresistive material 20, as described below). Sensor 10 is not limited to detecting concentrations of a target matter dispersed in the air. Sensor 10 can be used to measure a target matter concentration in a multitude of gas, liquid, and multiphase environments.

The reaction between the target matter and chemical: sensitive layer 30 may be caused by a variety of surface interactions between the chemical sensitive layer 30 and the target matter. These interactions may include, but are not limited to, adsorption (such as chemisorption and: physisorption) or related phenomena (or elements of multiple such phenomena). Chemical sensitive layer 30 may, be constructed and deposited so that its surface properties: differ from the bulk properties. Therefore, the interaction between the target matter and chemical sensitive layer 30 may be confined to the interface between the surface of chemical sensitive layer 30 and the target matter, even though the chemical species of the bulk of chemical sensitive layer 30 is identical to that of the surface.

Chemical sensitive layer 30 may be configured such that its thickness is thin enough so that adsorption of molecules of the target matter creates a surface tension at the interface of chemical sensitive layer 30 and piezoresistive material 20, but not thick enough such that a change in the bulk properties of chemical sensitive layer 30 affects the resistance of piezoresistive material 20 (for example, such that the target matter does not diffuse or absorb into chemical sensitive layer 30 enough to affect the resistance of piezoresistive material 20). For example, a mono-layer (one atom thick) chemical sensitive layer 30 may be used in particular embodiments. The adsorption of the target matter at the interface of chemical sensitive layer 30 and the target matter may create a surface tension at the interface of chemical sensitive layer 30 and piezoresistive material 20 (due to tension created at the interface of chemical sensitive layer 30 and the target matter). Furthermore, one or more target matter molecules may absorb or diffuse to the interface of chemical sensitive layer 30 and piezoresistive material 20 and replace one or more molecules of chemical sensitive layer 30 or piezoresistive material 20 at the interface. This replacement of molecules may be referred to as "surface reconstruction" and may also contribute to the interfacial tension described above, but without also causing a change in the bulk properties of chemical sensitive layer 30.

This interfacial tension is similar in certain respects to the surface tension of a liquid. This tension may be created without the introduction of a surface stress (or any other form of stress that can be measured) in layer 30 and without a change in the mechanical strain within the region coated with layer 30. Furthermore, the interaction of the target matter with the surface of the chemical sensitive layer 30 may not change the physical properties of layer 30, such as its molar volume, morphology, and the like, and may not lead to a change in the dimensions of the chemical sensitive layer 30. It also may not result in any mass loading, change in the surface charge density of chemical sensitive layer 30, or change in the membrane spring constant of layer 30.

Since chemical sensitive layer 30 is coupled to piezoresistive material 20, the interfacial tension imposed on the interface between chemical sensitive layer 30 and piezoresistive material 20 arising from the interaction with the target matter results in a change in resistance of piezoresistive material 20. This change in resistance of piezoresistive material 20 may then be measured by a third component of sensor 10, an electrical circuit 40, shown in FIG. 2.

The interfacial tension created in layer 30 may change significantly even when an extremely minute concentration of the target matter is present. This applied tension typically results in a change in resistance of the piezoresistive material at a specific rate. This rate of change in resistance may be used to indicate the concentration of the target matter that is interacting with chemical sensitive layer 30. The rate of change will be characteristic of the concentration of the target matter species and the nature of both the target matter species and the chemical sensitive layer 30 employed. Chemical sensitive layer 30 may be uniquely sensitive to a specific target matter and the rate of change of the resistance may be uniquely correlatable to a specific concentration of that target matter.

For selected cases, a series of chemical sensitive layers 30 may be selected to have a broad range of sensitivity, with each layer having sensitivities to more than one target matter. The rate of change in resistance, as well as its sign, for each selected chemical sensitive layer 30 in such a case may be a function of both multiple target matters and their concentrations. A unique identification of the respective target matters may be performed in this case by employing multiple sensors 10 each coated with a different chemical sensitive layer 30 with sensitivities to all of the target matters. Each individual target matter may then be detectable uniquely by examining the ratio of the rate of change of resistance between the multiple sensors 10.

FIG. 2 more clearly illustrates the use of electrical circuit 40 to detect the change in resistance of piezoresistive layer 30. Chemical sensitive layer 30 is not shown in FIG. 2 to more clearly show electrical circuit 40. Piezoresistive material 20 is electrically coupled to electrical circuit 40 through a pair of electrical leads 42. Electrical current may naturally flow through piezoresistive material 20, or it can be directed by electrical wiring 44. Any type of electrical circuit capable of detecting and/or measuring a change in resistance may be used in conjunction with piezoresistive material 20 and chemical sensitive layer 30.

It should be noted that the configuration of piezoresistive material 20 and chemical sensitive layer 30 in FIG. 1 is only one example of many different possible configurations. Piezoresistive material 20 is not required to cover an entire surface of support medium 22. In fact, such a configuration may not be desired for some applications. Piezoresistive material 20 is preferably placed in selected areas based on the interfacial tensions induced on the chemical sensitive layer 30 in response to the target material. For instance, piezoresistive material may be placed at locations where the applied tension is expected to be maximized.

Furthermore, chemical sensitive layer 30 does not have to entirely cover piezoresistive material 20. It may also be placed in more than one area to obtain configurations with enhanced sensitivity. In general, piezoresistive material 20 and chemical sensitive layer 30 are placed in relation to each other such that the interfacial tension imposed on the chemical sensitive layer 30 causes a change in resistance in piezoresistive material 20 that can be effectively detected and/or measured and associated with a corresponding concentration of the target matter.

Figure 3:
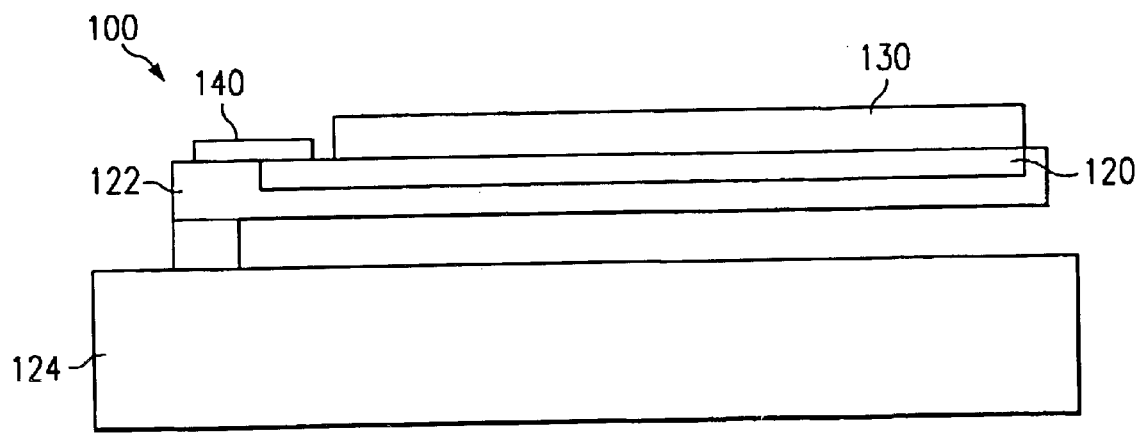
FIG. 3 is a schematic drawing in elevation showing portions of an example micro-electromechanical system for detecting very small concentrations of a selected target matter in accordance with teachings of the present invention.

FIG. 3 illustrates a sensor 100 representing another embodiment of the present invention. This embodiment may generally be described as a MEMS bulk micro-machined piezoresistive platform sensor with a chemical sensitive layer. Sensor 100 incorporates the same chemical sensitive/piezoresistive principles as sensor 10, shown in FIG. 1.

Sensor 100 includes a cantilevered beam 122 mounted on a substrate 124. Substrate 124 may perform at least two different functions. One such function may be to simply provide mechanical support for the cantilevered beam 122. Substrates performing this function may be fabricated from materials such as ceramics, plastics, glass, metals, or semiconductors such as silicon (Si), germanium (Ge), gallium arsenide (GaAs), aluminum gallium arsenide (AlGaAs), indium phosphide (InP), cadmium telluride (CdTe), or other Group III-V or II-VI semiconductor compounds. Another function that substrate 124 may perform is hosting electronic circuitry for acquiring and processing signals generated in the sensor. Substrates performing this function may be fabricated from materials such as silicon (Si), germanium (Ge), gallium arsenide (GaAs), aluminum gallium arsenide (AlGaAs), indium phosphide (InP), cadmium telluride (CdTe), silicon carbide (SiC), or other Group III-V or II-VI semiconductor compounds.

Beam 122 may serve as a support medium for one or more regions 120 of piezoresistive material implanted in beam 122. Piezoresistive regions 120 may comprise any type of piezoresistive material including, but not limited to, silicon doped with boron or phosphorus. However, the beam itself may also be comprised of piezoresistive material. Beam 122 may be made of appropriately doped silicon, Ge, GaAs, AlGaAs, SiC, diamond films, or conductive polymers such as polyimide/graphite composites.

A chemical sensitive layer 130 is coupled or bonded to piezoresistive layer 120. As described above in relation to FIG. 1, chemical sensitive layer 130 comprises a material specifically chosen such as to preferentially react with a target matter. Beam 122 may deform as a result of the interfacial tension imposed on the interface between piezoresistive layer 120 and chemical sensitive layer 130 when chemical sensitive layer 130 is exposed to the target matter. As beam 122 deforms, the resistance of piezoresistive layer 120 is changed. This change in resistance can then be detected and/or measured using an electrical circuit (not explicitly shown). This electrical circuit is coupled to piezoresistive layer 120 through the use of one or more bonding pads 140. Bonding pads 140 are used to support the wires of the electric circuit, and to maintain the connection of these wires to piezoresistive layer 120. Evaporated metals with low electrical conductivity may be used as bonding pads 140.

Figure 4:
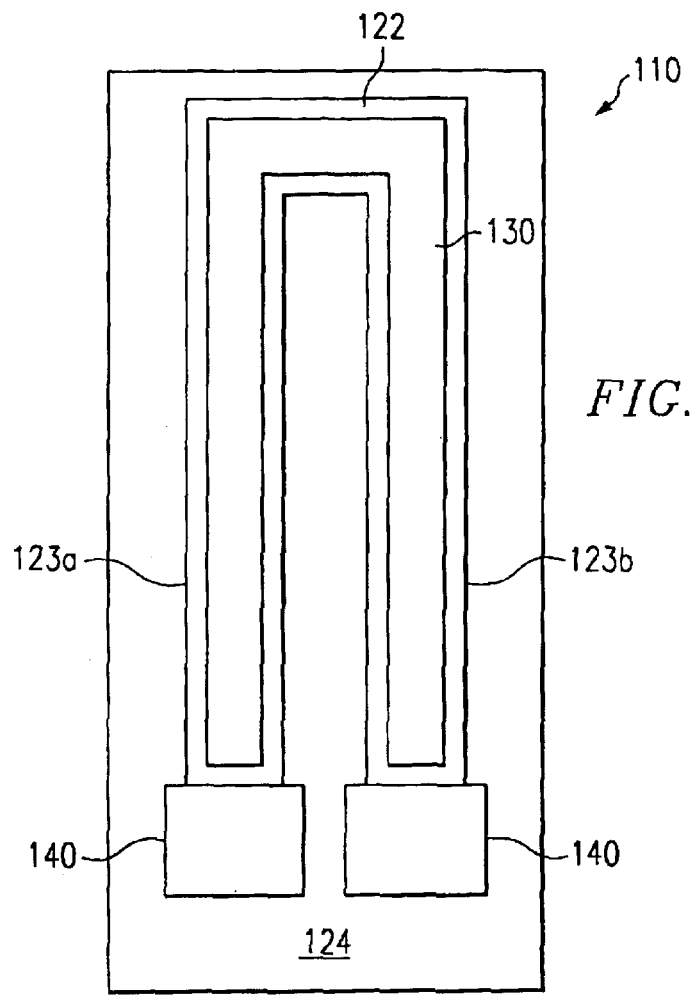
FIG. 4 is a plan view of a portion of the micro-electromechanical system of FIG. 3.

As shown in FIG. 4, a double beam cantilever shape may be employed that has two legs 123a and 123b. In this configuration, an electrical current directed into leg 123a will flow out of leg 123b, or the reverse. This current flow is used to measure the change in resistance of piezoresistive layer 120, and thus measure the concentration of the target matter. It should be noted that this "U"-shaped configuration is not required. The electrical current may be directed by other geometrical configurations, or the current may be conducted through the use of electrical wiring. It should also be noted that the cantilever configuration is also not a requirement. A membrane platform of any shape which is piezoresistive, including platforms hinged at both ends, may also function as sensors according to the teachings of the present invention.

Figure 5:
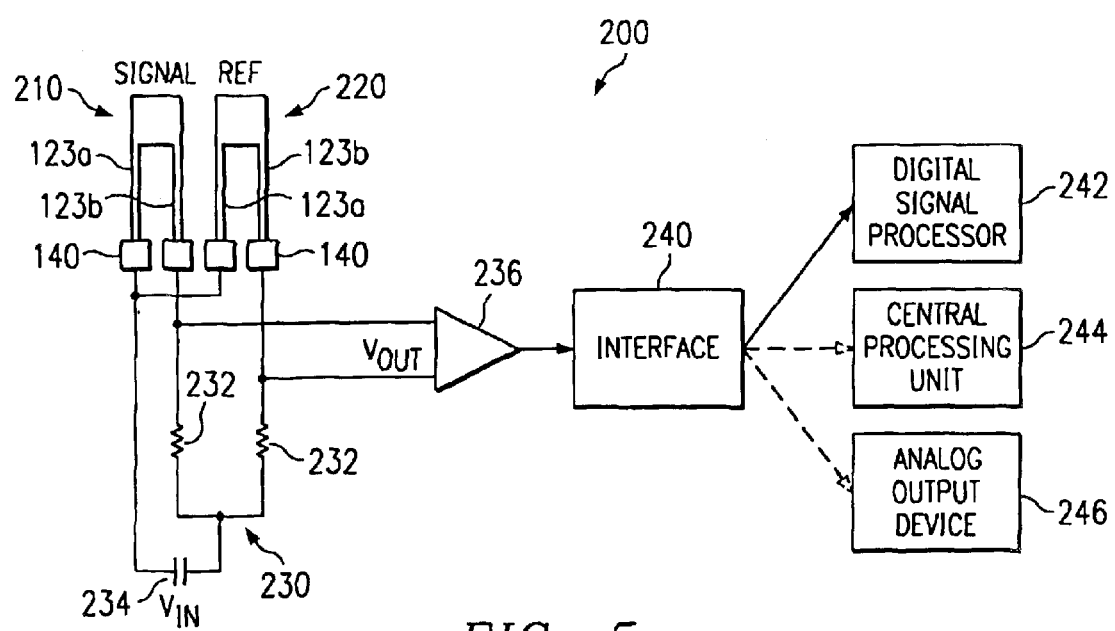
FIG. 5 is a schematic drawing of another example sensing system incorporating teachings of the present invention.

FIG. 5 shows a sensing system 200 incorporating teachings of the present invention. Sensing system 200 comprises two cantilevered beams. One beam is a signal beam 210 and the other is a reference beam 220. As shown in FIG. 5, beams 210 and 220 are "U"-shaped double cantilever beams, however, as indicated above, any type of beam or membrane supported in any way could also be used. As described above, the "U"-shaped beam may be used so that electrical current directed into one leg 123a of the "U" will flow out of the other leg 123b.

Signal beam 210 comprises one or more piezoresistive regions (not explicitly shown) and a chemical sensitive layer (not explicitly shown). However, reference beam 220 does not include a chemical sensitive layer. Reference beam 220 does include one or more piezoresistive regions (not explicitly shown).

Signal beam 210 and reference beam 220 are preferably coupled to an electrical circuit 230 through the use of bonding pads 140, as shown in FIG. 5. Electrical circuit 230 is used to detect and/or measure the change in resistance of the piezoresistive material of signal beam 210. Through the use of electrical circuit 230, the output of signal beam 210 is referenced to the output of reference beam 220. The use of a signal/reference pair eliminates system drift due to changes in ambient conditions in the monitoring environment. These ambient conditions include, but are not limited to, temperature, humidity, vibration, and the deposition of non-target matter.

In the embodiment shown in FIG. 5, electrical circuit 230 comprises a Wheatstone bridge that is used to measure the resistance change of signal beam 210. The configuration of a Wheatstone bridge is well known in the art, so it will not be described in detail here. The Wheatstone bridge includes four main sources of resistance. These sources of resistance are two resistors 232, signal beam 210, and reference beam 220. Signal beam 210 is connected in one arm of the Wheatstone bridge, and reference beam 220 is connected in another arm of the bridge. Electrical circuit 230 also includes a voltage source 234.

The change in resistance of the piezoresistive material of signal beam 210 is determined by measuring the output voltage of electrical circuit 230. Connecting reference beam 220 as one of the resistors eliminates common mode noise and interfering effects, and provides for an accurate measurement of the change in resistance of the piezoresistive material of signal beam 210.

Particular embodiments of the present invention may use a continuously and dynamically balanced Wheatstone bridge to maximize the sensitivity of the bridge and lower the change in resistance that can be detected and/or measured using the bridge. The sensitivity with which a change in resistance can be measured is maximized if the resistances on two arms are exactly balanced. The present embodiment employs a method by which these two resistances, one the sensor piezoresistor, the other a variable resistor, are always equal. The variable resistor may be programmed using a digital signal processor that continuously and dynamically varies the variable resistor's resistance to match the resistance of the piezoresistor. When a reference beam or a reference pizoresistor is employed, as described above, a second programmable variable resistor, using digital signal processing, may also be employed to exactly match its resistance.

The output voltage may be amplified using an amplifier 236. The amplified voltage reading is then sent, via an interface 240, to a digital or analog output device. Examples of such devices are a digital signal processor 242, a central processing unit 244, or an analog output device 246. The analog or digital output device may include a database that correlates a measured voltage or change in resistance with a certain concentration of the target matter. The analog or digital output device may then display or transmit the measured concentration to a user. Embodiments of the present invention may be used as dosimeters to measure the total exposure to a target matter, as well as being used as detectors. By integrating the signal response over time, the total degree of exposure to the target matter that reacts with a chemical sensitive layer in that time interval can be determined.

Furthermore, it should be understood that particular embodiments of the present invention may be used as a continuous monitoring detector to measure a change in the concentration of a target matter. Although the reaction of the target matter with the surface of the chemical sensitive layer may or may not be a reversible process, additional exposure can be measured as long as the surface of the chemical sensitive layer is not saturated. This will always be the mode during the operation of the present embodiment since the interaction of the target matter with the chemical sensitive layer will only be confined to the surface of the layer. In this continuous monitoring mode, a detector incorporating teachings of the present invention may make continuous samples over successive time intervals of a user-specified duration. The incremental change in resistance of the piezoresistive material is measured over the time interval. The output may then be specified in terms of a change in the target matter concentration over each time interval or as a total dose measurement by integrating the response over an extended period of time. A system incorporating the present invention is capable of detecting changes in concentration in the sub-ppt range.

Such continuous monitoring detectors may employ chemical sensitive layers with surface characteristics distinctly different from the characteristics of the bulk of the layers. The chemical processes between the target matter and the layer or layers will involve introducing interfacial tension on the surface of the layers. The nature of the interaction process could consist of, but not limited to, 1) activated adsorption without the participation of a precursor, 2) non-activated adsorption, or 3) activated adsorption with participation of a precursor. The first type of adsorption will typically be associated with an exponential increase in rate of change in resistance with increasing temperature, a continuous fall in rate of change with increasing coverage, and a rate of change that is directly proportional to the pressure of the target matter. The second type of adsorption will typically be associated with zero or negative temperature coefficient of rate of adsorption, with an initial rate of change of resistance independent of coverage, and with a rate of change that is proportional to the pressure of the target matter. The third type of adsorption will typically be associated with an exponential increase in rate of change of resistance with increase in temperature, a continuous fall in rate of change with increasing coverage, and with no simple dependence of rate of change on pressure (with proportionality to $\sqrt{p}$ being common).

For a given surface area of the chemical sensitive layer, saturation is proportional to the product of the target matter concentration and the exposure time. Thus, saturation is achieved when the surface of the chemical sensitive layer is fully reacted with the target matter and no more target matter can be adsorbed. As the ambient target matter concentration is decreased, the exposure time required for saturation increases. For example, a MEMS chemical sensitive membrane/platform detector, built according to teachings of the present invention, will last one thousand times longer when exposed to ambient target matter concentrations at the ppb level than when exposed to target matter concentrations at the ppm level.

In addition, sensors representing an embodiment of the present invention may be arranged in a multi-channel functional array (not explicitly shown). Such an array allows each individual sensor to have maximum sensitivity to a precise target matter. In this manner, an array may be used to detect a variety of different target matters. For example, an array could be used to detect a variety of different types of explosives and chemical weapon agents.

The present invention can theoretically be used to detect any type of target matter. The only requirement is that the surface of the chemical sensitive layer react with the target matter so as to apply an interfacial tension to the piezoresistive material. As examples only, the MEMS chemical sensitive detector shown in FIGS. 3 and 4, has been used to demonstrate detection of mercury (Hg) vapor and volatile organic compounds (VOCs) such as alcohols, acetone, and benzene with sub-ppt sensitivity. In the case of mercury vapor detection, the chemical sensitive layer used can be a thin gold (Au) film (for example, 1000 Angstroms) having surface properties that differ substantially from its bulk. The objective of having the bulk properties differ significantly from those of the surface may be fulfilled in this case even though both the surface and the bulk are constructed out of the same material (gold).

Experimentation using such a gold chemical sensitive layer has produced the following results. For the concentrations of mercury vapor employed, using a source of condensed mercury held in dewar with temperatures controlled to stay below −56° Celsius, such that the mercury vapor concentrations stayed below 90 ppt, the interaction between the mercury vapor and the gold layer remained exclusively confined to the surface without leading to a change in the volume and/or structural property of the gold layer itself, and without any mass loading that could be measured. The mercury vapor pressures could be progressively reduced by lowering the dewar temperature, and it was possible to detect mercury vapor present at a concentration of 0.03 ppt within thirty seconds. The corresponding dewar temperature was −92° Celsius. In the case of VOC detection, very thin layers of photoresist can be used as the chemical sensitive layer. For very small concentrations of these target matter vapors, the interaction between the target matter and the chemical sensitive layers is confined to the interface without any volume and/or structural changes of the chemical sensitive layer itself. These interactions will produce an interfacial tension.

Although the present invention and its advantages have been described in detail, it should be understood that various changes, substitutions, and alterations can be made therein without departing from the spirit and scope of the present invention as defined by the appended claims.

What is claimed is:

1. A sensor for detecting a target matter, the sensor comprising:
    a chemical sensitive layer operable to react when exposed to the target matter;
    a piezoresistive material coupled to the chemical sensitive layer;
    the chemical sensitive layer having a thickness thin enough such that adsorption of the target matter into the chemical sensitive layer creates an interfacial tension at the interface of the chemical sensitive layer and the piezoresistive material that changes the electrical resistance of the piezoresistive material, but thick enough such that the reaction of the target matter with the chemical sensitive layer does not affect the bulk properties of the chemical sensitive layer enough to change the electrical resistance of the piezoresistive material; and
    an electrical circuit coupled to the piezoresistive material operable to detect the change in the electrical resistance of the piezoresistive material due to the interfacial tension.

2. The sensor of claim 1, wherein the electrical circuit is further operable to detect the rate of change in the electrical resistance of the piezoresistive material to determine the concentration of the target matter.

3. The sensor of claim 1, wherein the electrical circuit is further operable to detect the rate of change in the electrical resistance of the piezoresistive material to determine the type of target matter.

4. The sensor of claim 1, wherein the chemical sensitive layer is configured such that the reaction of the target matter with the chemical sensitive layer does not change the dimensions of the chemical sensitive layer.

5. The sensor of claim 1, wherein the chemical sensitive layer is a mono-layer.

6. The sensor of claim 1, wherein the electrical circuit comprises a Wheatstone bridge.

7. The sensor of claim 6, wherein the Wheatstone bridge comprises at least two resistors, the piezoresistive material and a variable resistor.

8. The sensor of claim 7, wherein the electrical circuit further comprises a digital signal processor operable to dynamically vary the electrical resistance of the variable resistor to match the resistance of the piezoresistive material.

9. The sensor of claim 1, wherein the target matter comprises mercury and the chemical sensitive layer comprises gold.

10. The sensor of claim 1, wherein the target matter comprises a volatile organic compound and the chemical sensitive layer comprises photoresist.

11. A method of detecting a target matter comprising:
    forming a chemical sensitive layer selected to react when exposed to the target matter;
    coupling the chemical sensitive layer to a piezoresistive material, the chemical sensitive layer configured such that the reaction of the target matter with the chemical sensitive layer creates an interfacial tension at the interface of the chemical sensitive layer and the piezoresistive material that changes the electrical resistance of the piezoresistive material, but such that the reaction of the target matter with the chemical sensitive layer does not affect the bulk properties of the chemical sensitive layer enough to change the electrical resistance of the piezoresistive material;
    exposing the chemical sensitive layer to the target matter; and
    detecting a change in the electrical resistance of the piezoresistive material due to the interfacial tension.

12. The method of claim 11, further comprising correlating the measured change in resistance of the piezoresistive material with a corresponding concentration of the target matter.

13. The method of claim 11, further comprising correlating the measured change in resistance of the piezoresistive material with a corresponding type of target matter.

14. The method of claim 11, wherein the chemical sensitive layer is formed such that it has a thickness thin enough such that adsorption of the target matter into the chemical sensitive layer creates a interfacial tension at the interface of the chemical sensitive layer and the piezoresistive material.

15. The method of claim 11, wherein the chemical sensitive layer is formed such that it has a thickness thick enough such that the target matter does not affect the bulk properties of the chemical sensitive layer enough to change the electrical resistance of the piezoresistive material.

16. The method of claim 11, wherein the chemical sensitive layer is formed such that the reaction of the target matter with the chemical sensitive layer does not change the dimensions of the chemical sensitive layer.

17. The method of claim 11, wherein the chemical sensitive layer is a mono-layer.

18. The method of claim 11, wherein the change in electrical resistance is detected using a Wheatstone bridge.

19. The method of claim 18, wherein the Wheatstone bridge comprises at least two resistors, the piezoresistive material and a variable resistor.

20. The method of claim 19, further comprising dynamically varying the electrical resistance of the variable resistor to match the resistance of the piezoresistive material.

21. A sensor for detecting a target matter, the sensor comprising:

a chemical sensitive layer operable to react when exposed to the target matter;

a piezoresistive material coupled to the chemical sensitive layer;

the chemical sensitive layer having a thickness thin enough such that adsorption of the target matter into the chemical sensitive layer creates an interfacial tension at the interface of the chemical sensitive layer and the piezoresistive material that changes the electrical resistance of the piezoresistive material, but thick enough such that the reaction of the target matter with the chemical sensitive layer does not affect the bulk properties of the chemical sensitive layer enough to change the electrical resistance of the piezoresistive material;

an electrical circuit coupled to the piezoresistive material operable to detect the change in the electrical resistance of the piezoresistive material due to the interfacial tension; and wherein the electrical circuit comprises a digital signal processor operable to dynamically vary the electrical resistance of the variable resistor to match the resistance of the piezoresistive material and a Wheatstone bridge that comprises at least two resistors, the piezoresistive material, and a variable resistor.

22. A method of detecting a target matter comprising:

exposing a chemical sensitive layer to the target matter;

creating, by reaction of the chemical sensitive layer with the target matter, an interfacial tension at an interface of the chemical sensitive layer and a piezoresistive material that changes the electrical resistance of the piezoelectrical material without affecting the bulk properties of the chemical sensitive layer enough to change the electrical resistance of the piezoresistive material; and detecting a change in the electrical resistance of the piezoresistive material due to the created interfacial tension.

* * * * *